(12) United States Patent
Inoue et al.

(10) Patent No.: US 10,441,143 B2
(45) Date of Patent: Oct. 15, 2019

(54) INSERTION ASSISTING TOOL FOR ENDOSCOPE

(71) Applicant: FUJIFILM Corporation, Tokyo (JP)

(72) Inventors: Masaya Inoue, Ashigarakami-gun (JP); Masayuki Iwasaka, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/969,404

(22) Filed: May 2, 2018

(65) Prior Publication Data

US 2018/0249897 A1 Sep. 6, 2018

Related U.S. Application Data

(60) Division of application No. 14/039,902, filed on Sep. 27, 2013, now Pat. No. 9,986,897, which is a
(Continued)

(30) Foreign Application Priority Data

Mar. 31, 2011 (JP) ................. 2011-079218

(51) Int. Cl.
*A61B 1/00* (2006.01)
*E05D 7/081* (2006.01)
*G02B 23/24* (2006.01)

(52) U.S. Cl.
CPC ...... *A61B 1/00147* (2013.01); *A61B 1/00098* (2013.01); *A61B 1/00154* (2013.01);
(Continued)

(58) Field of Classification Search
CPC ................................................. A61B 1/00098
See application file for complete search history.

(56) References Cited

U.S. PATENT DOCUMENTS

| 4,224,929 A | 9/1980 | Furihata |
| 4,982,724 A | 1/1991 | Saito et al. |

(Continued)

FOREIGN PATENT DOCUMENTS

| EP | 1 836 966 A1 | 9/2007 |
| EP | 1 955 643 A1 | 9/2007 |

(Continued)

OTHER PUBLICATIONS

Extended European Search Report, dated Jul. 22, 2014, for European Application No. 12763908.6.
(Continued)

*Primary Examiner* — Aaron B Fairchild
(74) *Attorney, Agent, or Firm* — Birch, Stewart, Kolasch & Birch, LLP

(57) ABSTRACT

Operability in inserting an insertion part of an endoscope into a body cavity using an insertion assisting tool is improved. In an insertion assisting tool 60, a sidewall portion of a tube main body 64 through which an insertion part 12 of an endoscope 10 is passed is provided with a sidewall opening part 68 having a size in which the insertion part 12 can pass through. A distal end side of the sidewall opening part 68 is provided with a guiding valve 82, and the insertion part 12 is guided by the guiding valve 82 to be easily fed from the sidewall opening part 68. The guiding valve 82 is swingably supported, and when the insertion part 12 is fed from a distal end opening part 67 of the tube main body 64, allowing the parallel state of being substantially parallel to an axial direction of the insertion part 12 and passing the insertion part 12 to a distal end opening part 67 side are enabled.

2 Claims, 13 Drawing Sheets

Related U.S. Application Data continuation of application No. PCT/JP2012/055618, filed on Mar. 6, 2012.

(52) U.S. Cl.
CPC .......... *A61B 1/00082* (2013.01); *E05D 7/081* (2013.01); *G02B 23/2476* (2013.01)

(56) References Cited

U.S. PATENT DOCUMENTS

| | | | |
|---|---|---|---|
| 5,152,277 | A | 10/1992 | Honda et al. |
| 5,460,168 | A * | 10/1995 | Masubuchi ........ A61B 1/00098 600/107 |
| 2005/0090709 | A1 | 4/2005 | Okada et al. |
| 2005/0131278 | A1 | 6/2005 | Dickopp |
| 2007/0213632 | A1 | 9/2007 | Okazaki et al. |
| 2007/0249898 | A1 | 10/2007 | Otawara |
| 2008/0249356 | A1 | 10/2008 | Motai et al. |
| 2008/0287961 | A1 | 11/2008 | Miyamoto et al. |
| 2010/0228086 | A1 | 9/2010 | Ohki et al. |
| 2010/0313482 | A1 | 12/2010 | Minegishi et al. |
| 2012/0238815 | A1 | 9/2012 | Komi et al. |

FOREIGN PATENT DOCUMENTS

| | | |
|---|---|---|
| JP | 60-185532 A | 9/1985 |
| JP | 62-292135 A | 9/1985 |
| JP | 62-22623 A | 1/1987 |
| JP | 2010-253234 A | 11/2010 |
| JP | 2011-10810 A | 1/2011 |
| JP | 2011-131047 A | 7/2011 |
| WO | WO 2006-038634 A1 | 4/2006 |

OTHER PUBLICATIONS

International Preliminary Report on Patentability and Written Opinion of the International Searching Authority with English language translation (Forms PCT/IB/338, PCT/IB/373, PCT/ISA/237 and PCT/IB/326), dated Oct. 10, 2013, for International Application No. PCT/JP2012/055618.
International Search Report issued in PCT/JP2012/055618, dated Jun. 5, 2012.
Japanese Office Action and partial English translation dated Sep. 17, 2014 for Application No. 2011-079218.
Japanese Office Action and partial English translation thereof, dated Jan. 30, 2014, for Japanese Application No. 2011-079218.
PCT/ISA/237—Mailed on June 5, 2012, issued in PCT/JP2012/055618.
Official Communication dated Jul. 10, 2017 in corresponding European Patent Application No. 12763908.6.
Official Communication dated Oct. 21, 2016 in corresponding European Patent Application No. 12763908.6.
U.S. Notice of Allowance dated Feb. 6, 2018 in U.S. Appl. No. 14/039,902.
U.S. Office Action dated Apr. 21, 2017 in U.S. Appl. No. 14/039,902.
U.S. Office Action dated Apr. 29. 2016 in U.S. Appl. No. 14/039,902.
U.S. Office Action dated Jan. 21, 2016 in U.S. Appl. No. 14/039,902.
U.S. Office Action dated Nov. 1, 2017 in U.S. Appl. No. 14/039,902.
U.S. Office Action dated Oct. 28, 2016 in U.S. Appl. No. 14/039,902.
Extended European Search Report for corresponding European Application No. 18205759.6, dated Feb. 15, 2019.

\* cited by examiner

INSERTION ASSISTING TOOL FOR ENDOSCOPE

CROSS-REFERENCE TO RELATED APPLICATIONS

This application is a divisional of U.S. application Ser. No. 14/039,902, filed Sep. 27, 2013, which is a continuation application and claims the priority benefit under 35 U.S.C. § 120 of PCT Application No. PCT/JP2012/055618 filed on Mar. 6, 2012, of which application designates the U.S., and also claims the priority benefit under 35 U.S.C. § 119 of Japanese Patent Application No. 2011-079218 filed on Mar. 31, 2011, all of which are hereby expressly incorporated by reference into the present application.

TECHNICAL FIELD

The present invention relates to an insertion assisting tool for an endoscope, and in particular, relates to an insertion assisting tool for an endoscope used in inserting an insertion part of an endoscope into the biliary tract or the pancreatic duct.

BACKGROUND ART

In recent years, endoscopic examination or treatment of pancreaticobiliary diseases such as biliary tract cancer, pancreas cancer, cholelithiasis and choledocholithiasis, for example, has been widely spreading in the field of medicine. These have the advantages of being less invasive and imposing less strain on patients than conventional surgical treatment.

As one method for these examination and treatment, for example, there is known ERCP (Endoscopic Retrograde Cholangio-Pancreatography). The ERCP is a diagnosis method using an endoscope to inject contrast medium into the biliary tract or the pancreatic duct and photograph that portion with a fluoroscope. In the method of injecting the contrast medium, first, an insertion part of the endoscope is inserted into the duodenum. Then, a cannula (thin tube) is fed from a forceps exit of the insertion part, the cannula is inserted from the major duodenal papilla selectively into the biliary tract or the pancreatic duct, a contrast medium is injected into the biliary tract or the pancreatic duct through the cannula, and that portion is photographed with a fluoroscope.

Moreover, a method of confirming the presence or absence of a site of stenosis inside the biliary tract or the pancreatic duct, sampling and examining cells or tissues (cytodiagnosis and biopsy), removing calculi, or the like is also known, which is performed by inserting the insertion part of a thin endoscope, generally called cholangioscope or pancreatoscope, into the biliary tract or the pancreatic duct.

Under these circumstances, when the insertion part of the endoscope is inserted into a body cavity, an insertion assisting tool for an endoscope (also called "overtube" or "sliding tube") is used together. As one example of the insertion assisting tool for an endoscope, PTL 1 discloses one including a tubular body used as a guide through which an insertion part of an endoscope is passed, an opening part through which a distal end of the insertion part can be passed, the opening part being provided on a distal end side of a sidewall portion of the tubular body. According to this insertion assisting tool for an endoscope, when the insertion part of the endoscope is inserted into a body cavity, it is made possible by performing insertion in a state where the insertion part is covered with the tubular body easily, to perform insertion operation of the insertion part while preventing excessive bending or flexing of the insertion part. Moreover, when the distal end of the insertion part is fed from the opening part of the sidewall portion of the tubular body to be guided into a body cavity (for example, into the biliary tract), the insertion part can be easily put forward into a deep portion in the body cavity by performing the insertion while the insertion part is received and supported on an edge portion of the opening part.

Moreover, PTL 2 discloses one including an inflatable and deflatable balloon that is positioned more distally than the opening part formed in the sidewall portion of the tubular body. According to this insertion assisting tool for an endoscope, after the insertion part covered with the tubular body as mentioned above, is inserted up to a desired position in the body cavity, by inflating the balloon so as to come into close contact with an inner wall of the body cavity, the opening part of the sidewall portion can be held at a desired position (for example, at a position opposite to the major duodenal papilla). Moreover, when the distal end of the insertion part of the endoscope is fed from the opening part and the distal end of the insertion part is made into a J-shape and guided onto a proximal end side of the insertion part (for example, into the biliary tract), since the insertion part is guided while received and supported on an upper face of the balloon, the insertion part can be easily put forward.

CITATION LIST

Patent Literature

{PTL 1} Japanese Patent Application Laid-Open No. 60-185532
{PTL 2} Japanese Patent Application Laid-Open No. 62-22623

SUMMARY OF INVENTION

Technical Problem

However, in the conventional insertion assisting tools for an endoscope disclosed in PTL 1 and PTL 2, for the purpose of smoothly feeding the distal end of the insertion part from the opening part of the sidewall portion of the tubular body, since expertise is needed in operation of the endoscope, in particular, bending operation of a bending part, there is a problem that manipulation cannot easily be performed.

The present invention has been made in view of these circumstances, and an object of the present invention is to provide an insertion assisting tool for an endoscope capable of allowing an insertion part of an endoscope smoothly and easily to be fed from an opening part of a sidewall portion of a tubular body.

Solution to Problem

In order to achieve the object, an insertion assisting tool for an endoscope according to the present invention includes: a tubular body having a passage through which an insertion part of an endoscope is passed; a sidewall opening part provided on a distal end side of a sidewall portion of the tubular body, a distal end portion of the insertion part being capable of passing through the sidewall opening part; and a guiding member disposed in the passage and having a guiding surface guiding the insertion part inserted into the passage to a distal end side of the sidewall opening part, wherein the guiding member is a movable guiding member capable of transition between an inclined state where the guiding surface is obliquely inclined relative to an axial direction of the tubular body and a retracted state where the guiding surface is made substantially parallel to the axial direction of the tubular body, and the guiding surface is capable of guiding the insertion part to the sidewall opening part in the inclined state out of the inclined state and the retracted state.

According to the present invention, since the guiding member guiding the insertion part of the endoscope to the sidewall opening part is provided, even an inexperienced operator in bending operation of the endoscope can smoothly and easily feed the insertion part from the sidewall opening part.

In the present invention, it is preferable that the guiding surface be configured to be rotatable between the inclined state and the retracted state, a supporting part which is supported on the sidewall portion of the tubular body being a center axis.

In the present invention, it is preferable that an end portion of the guiding member on a side of the supporting part be disposed more proximally than a distal end of the sidewall opening part.

In the present invention, it is preferable that the supporting part be provided at a position in a vicinity of the sidewall opening part. According to the present invention, the configuration is such that the end portion of the guiding surface on the supporting part side is disposed on the distal end side of the tubular body (sidewall opening part) and that the end portion of the guiding surface on the side opposite to the supporting part side is disposed on the proximal end side of the tubular body.

In the present invention, it is preferable to include manipulating means capable of switching the guiding surface between the inclined state and the retracted state. According to the present invention, by switching the guiding surface between the inclined state and the retracted state with the manipulating means, insertion operation of the insertion part is easily to be performed in either case where the insertion part is fed or not fed from the sidewall opening part.

In the present invention, it is preferable to include biasing means for urging the guiding surface in a direction in which the guiding surface is allowed to progress from any one state of the inclined state and the retracted state to another state, wherein the manipulating means is means for manipulating the guiding surface in a direction opposite to a direction in which the urging means urges the guiding surface. According to the present invention, by including the urging means for urging toward any one state of the inclined state and the retracted state, the manipulation direction in which the manipulating means manipulates the guiding member may be one direction, enabling to reduce load on manipulation of the guiding member.

In the present invention, it is preferable that an inflatable and deflatable balloon be disposed on an outer peripheral surface of the tubular body that is positioned more distally than the sidewall opening part. According to the present invention, by inflating the balloon to allow it to come into contact with a wall surface in the body cavity, a position of the sidewall opening part can be held in a stable state, and the insertion part fed from the sidewall opening part can easily be guided to an expected position.

In the present invention, it is preferable that the guiding member come in contact with an inner surface of the sidewall portion on a side opposite to the sidewall opening part of the tubular body in the inclined state.

In the present invention, it is preferable that the guiding member be a foldable member and be a movable guiding member capable of transition between the inclined state and the retracted state in response to pushing force of the insertion part.

Advantageous Effects of Invention

According to the present invention, the insertion part of the endoscope can be smoothly and easily fed from the opening part in the sidewall portion of the tubular body.

DESCRIPTION OF EMBODIMENTS

Hereafter, preferred embodiments of the present invention will be described in detail according to the accompanying drawings.

Figure 1:
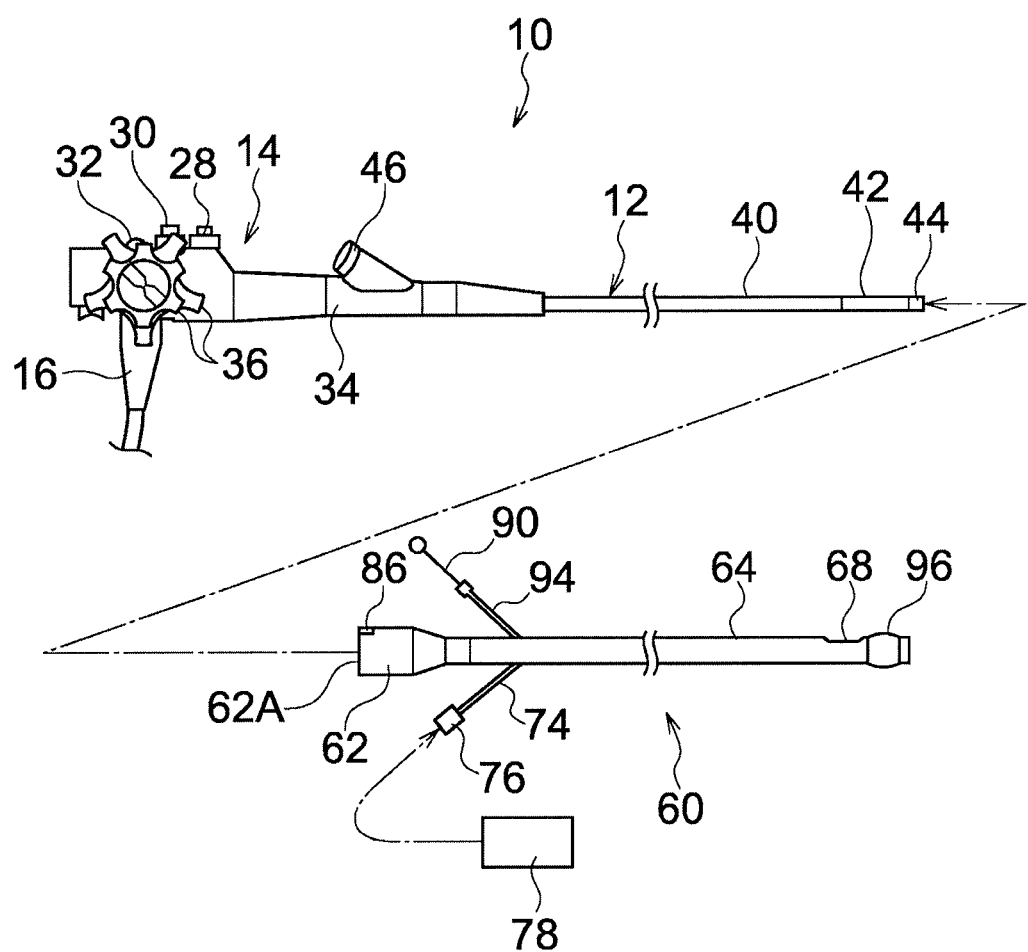
FIG. 1 is an external view showing an endoscopic device to which an insertion assisting tool according to an embodiment of the present invention is applied.

FIG. 1 is an external view showing an endoscopic device to which an insertion assisting tool for an endoscope (hereinafter simply referred to as "insertion assisting tool") 60 according to an embodiment of the present invention is applied. As shown in FIG. 1, the endoscopic device is mainly composed of an endoscope 10 and the insertion assisting tool 60.

The endoscope 10 includes a hand operating part 14 and an insertion part 12 that is provided in connection with this hand operating part 14 and inserted into the body. The hand operating part 14 is connected to a universal cable 16 and a distal end of this universal cable 16 is provided with a light guide (LG) connector (not shown in the figure). The LG connector is attachably and detachably coupled with a light source device (not shown in the figure) by which illumination light is transmitted to an illumination optical system 54 (see FIG. 2) mentioned later. Moreover, the LG connector is connected to an electric connector and this electric connector is attachably and detachably coupled with a processor performing image signal processing or the like.

The hand operating part 14 is provided with an air-supply/water-supply button 28, a suction button 30 and a shutter button 32, which are positioned side by side, and also provided with a pair of angle knobs 36, 36.

The insertion part 12 is composed of a flexible part 40, a bending part 42 and a distal end portion 44 in this order from the hand operating part 14 side, and the bending part 42 remotely undergoes bending operation by rotating the angle knobs 36, 36 of the hand operating part 14. This makes it possible to turn the distal end portion 44 to a desired direction.

Figure 2:
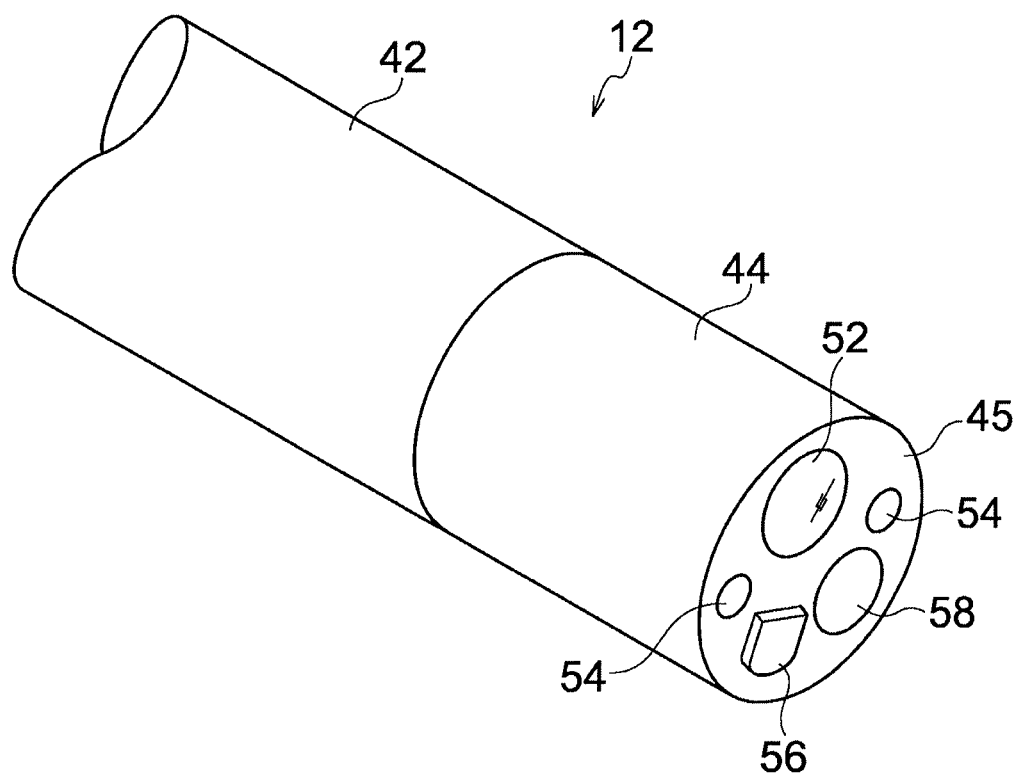
FIG. 2 is a perspective view showing a distal end part of an insertion part of an endoscope.

As shown in FIG. 2, a distal end face 45 of the distal end portion 44 is provided with an observation optical system 52, the illumination optical systems 54, an air-supply/water-supply nozzle 56 and a forceps exit 58. A CCD (not shown) is disposed behind the observation optical system 52 and a substrate supporting this CCD is connected to a signal cable (not shown). The signal cable is extended to the electrical connector through the insertion part 12, the hand operating part 14, the universal cable 16 and the like in FIG. 1 to be connected to the processor. Therefore, an observation image taken by the observation optical system 52 is imaged on a light-receiving surface of the CCD and converted into an electric signal, and then, this electric signal is outputted to the processor via the signal cable and converted into a video signal. Thereby, the observation image is displayed on a monitor connected to the processor.

A light emission end of a light guide (not shown) is disposed behind the illumination optical systems 54, 54 in FIG. 2. This light guide is passed through the insertion part 12, the hand operating part 14 and the universal cable 16 in FIG. 1, and an incident end thereof is disposed in the LG connector. Accordingly, by coupling the LG connector with the light source device, illumination light emitted from the light source device is transmitted to the illumination optical systems 54, 54 via the light guide and emitted forward from the illumination optical systems 54, 54.

The air-supply/water-supply nozzle 56 in FIG. 2 is in communication with a valve (not shown) operated with the air-supply/water-supply button 28 in FIG. 1, and this valve is further in communication with an air-supply/water-supply connector (not shown) provided in the LG connector. Air-supply/water-supply means not shown in the figures is connected to the air-supply/water-supply connector to supply air and water. Accordingly, by operating the air-supply/water-supply button 28, air or water can be sprayed from the air-supply/water-supply nozzle 56 toward the observation optical system 52.

The forceps exit 58 in FIG. 2 is in communication with a forceps entrance 46 in FIG. 1 via a forceps channel (not shown). Therefore, by inserting a treatment instrument such as forceps through the forceps entrance 46, this treatment instrument can be fed from the forceps exit 58. Moreover, the forceps exit 58 is in communication with a valve (not shown) operated with the suction button 30, and this valve is further connected to a suction connector (not shown) of the LG connector. Accordingly, suction means not shown in the figures is connected to the suction connector and the valve is operated with the suction button 30, so that a site of lesion or the like can be sucked through the forceps exit 58.

On the other hand, the insertion assisting tool 60 shown in FIG. 1 includes a grasping part 62 and a tube main body 64. The tube main body 64 is formed into a tubular shape and has an inner diameter larger than an outer diameter of the insertion part 12 such that the insertion part 12 of the endoscope 10 can be passed through it. Moreover, the tube main body 64 is a flexible molded product made of urethane-based resin, an outer peripheral surface thereof is coated with lubricant and an inner peripheral surface thereof is also coated with lubricant. The grasping part 62 shown in FIG. 1, which is hard, is fitted on the tube main body 64 in the water-tight state, and the grasping part 62 is attachably and detachably coupled with the tube main body 64. In addition, the insertion part 12 is inserted into the tube main body 64 from a proximal end opening part 62A of the grasping part 62.

Figure 3:
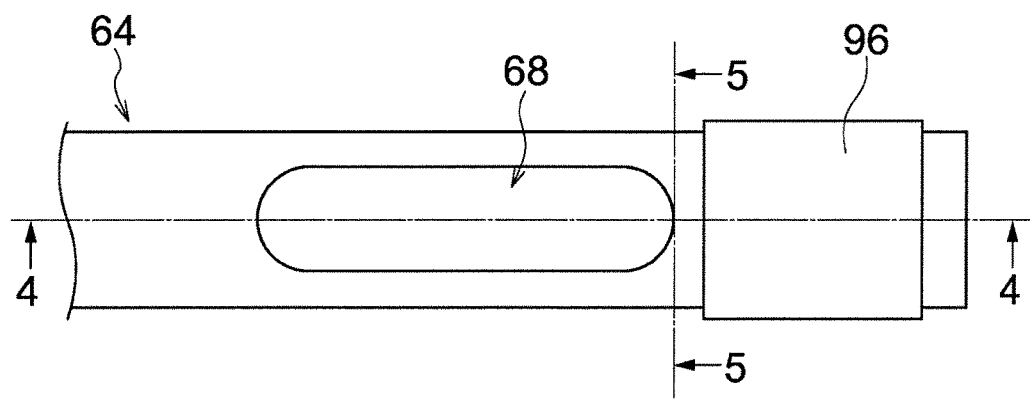
FIG. 3 is a schematic diagram (plan view) showing an exemplary configuration in the vicinity of a distal end of the insertion assisting tool.
Figure 4:
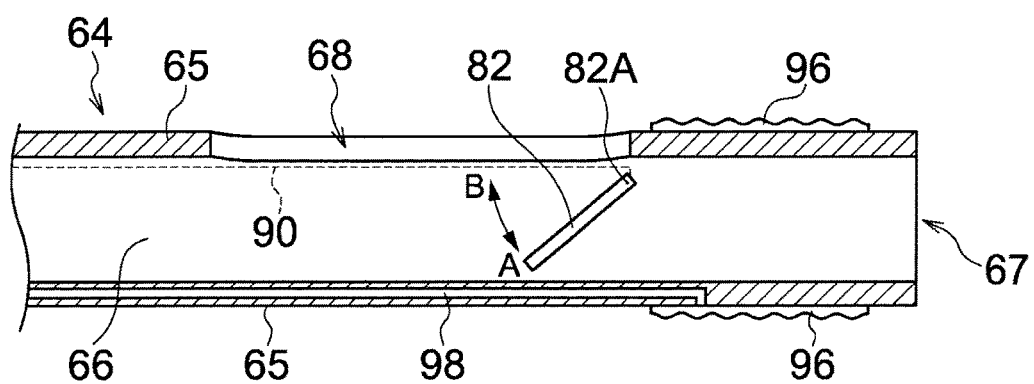
FIG. 4 is a schematic diagram (lateral cross-sectional view) showing an exemplary configuration in the vicinity of the distal end of the insertion assisting tool.
Figure 5:
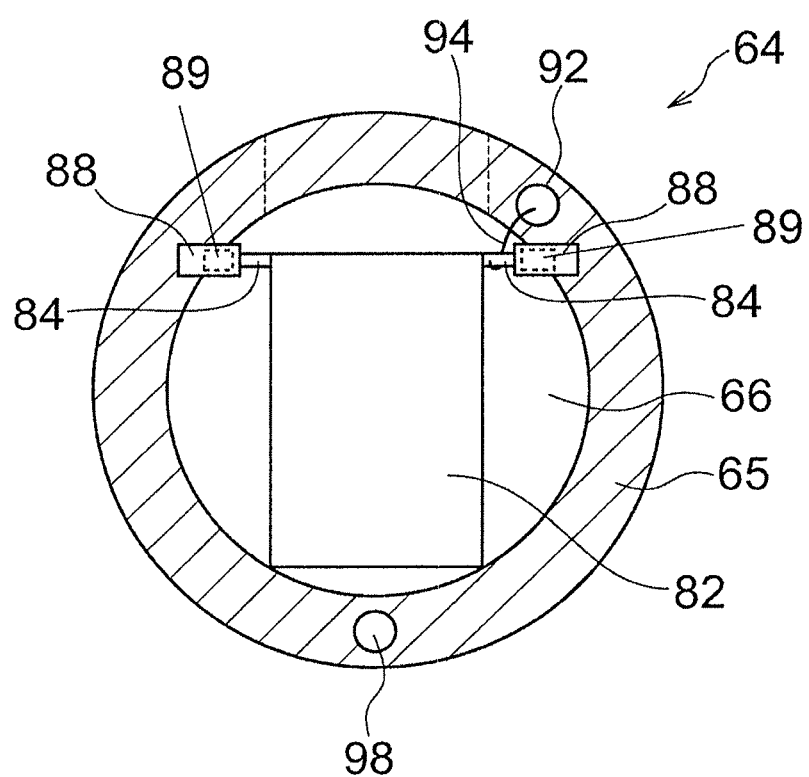
FIG. 5 is a schematic diagram (cross-sectional view) showing an exemplary configuration in the vicinity of the distal end of the insertion assisting tool.

Herein, a configuration of the tube main body 64 is described in detail. FIG. 3 to FIG. 5 are schematic views showing an exemplary configuration of the vicinity of a distal end of the tube main body 64, in which FIG. 3 is a plan view thereof, FIG. 4 is a lateral cross-sectional view (cross-sectional view taken along line 4-4 in FIG. 3) thereof, and FIG. 5 is a cross-sectional view (cross-sectional view taken along line 5-5 in FIG. 3) thereof.

As shown in FIG. 3 to FIG. 5, a passage 66 is provided to extend along an axis of the tube main body 64 inside the tube main body 64, and openings which are end parts of the passage 66 are formed at a distal end and a proximal end of the tube main body 64. Hereinafter, the opening at the distal end is referred to as a distal end opening part 67.

The passage 66 is a channel through which the insertion part 12 of the endoscope 10 (see FIG. 1) is passed, and a cross-sectional shape thereof perpendicular to the axis direction is formed into a substantially circular shape. When the insertion part 12 of the endoscope 10 is inserted through the proximal end opening part 62A of the grasping part 62 in FIG. 1, the insertion part 12 progresses into the passage 66 from the opening at the proximal end of the tube main body 64, and when the insertion part 12 is allowed to progress further along the passage 66, the insertion part 12 is passed through the inside of the passage 66 and can be fed from the distal end opening part 67 of the tube main body 64.

A sidewall portion 65 on the distal end side of the tube main body 64 is provided with an opening part 68 composed of a through hole with an oval shape in which the axial direction of the tube main body 64 is its longitudinal direction (hereinafter referred to as sidewall opening part 68). This sidewall opening part 68 is a hole part having a size at which the insertion part 12 passed through the passage 66 can pass through it, and is formed such that an opening width of the opening part 68 (length thereof in a direction perpendicular to the axial direction of the tube main body 64) is slightly larger than the outer diameter of the insertion part 12 of the endoscope 10 (diameter) and a length thereof (length in the axial direction of the tube main body 64) is sufficiently larger than the opening width. Thereby, as mentioned later, by performing bending operation of the insertion part 12 inserted into the passage 66 of the tube main body 64, the distal end of the insertion part 12 can be fed to the outside through the sidewall opening part 68 of the tube main body 64. In addition, it is preferable to provide an index 86 (see FIG. 1) indicating the direction of the sidewall opening part 68 in the grasping part 62.

Moreover, the passage 66 of the tube main body 64 is provided with a guiding valve 82 swingably supported at a position in the vicinity of the distal end of the sidewall opening part 68, a direction perpendicular to the axial direction of the tube main body 64 being a supporting axis 82A. The guiding valve 82 is formed into a plate shape, and as shown in FIG. 5, shaft pins 84, 84 protrude on both side faces on the proximal end side thereof. These shaft pins 84 are rotatably supported on shaft receiving members 88, 88 embedded in the sidewall portion 65 of the tube main body 64, while urged in a predetermined rotation direction by a helical torsion coil spring 89, for example, intervening between the shaft receiving members 88, 88 and the shaft pins 84, 84. In the view illustrated FIG. 5, the helical torsion spring 89 would be hidden from view and is thus illustrated with broken lines in the figure.

In addition, it is preferable to provide the guiding valve 82 at a position where the end part of the guiding valve 82 on the supporting axis 82A side is positioned more proximally than the end part of the sidewall opening part 68 on its distal end side.

Figure 6A:
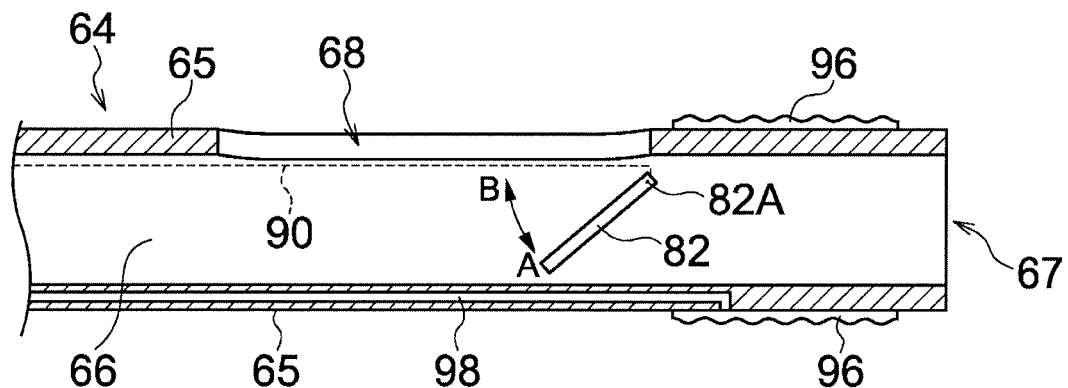
FIG. 6A is an explanatory drawing (lateral cross-sectional view) used for describing action of a guiding valve of the insertion assisting tool.
Figure 6B:
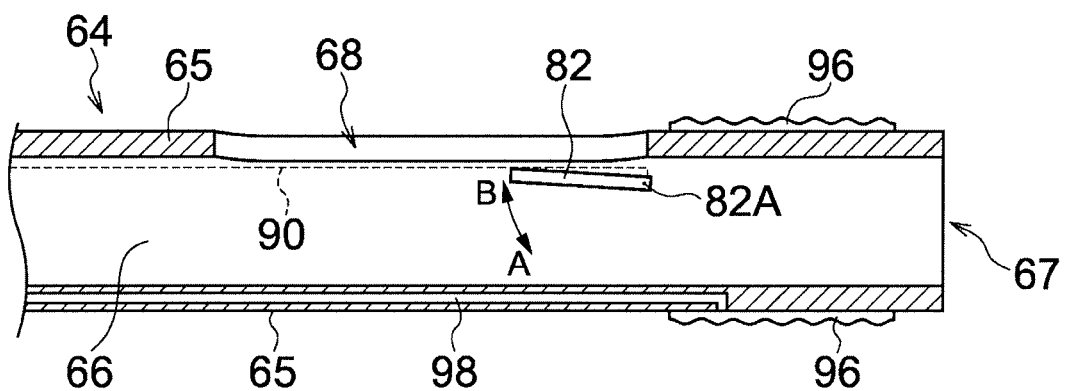
FIG. 6B is an explanatory drawing (lateral cross-sectional view) used for explaining action of a guiding valve of the insertion assisting tool.

Thereby, with the position of the shaft pins 84 being the supporting axis 82A (fulcrum) as shown in FIG. 4, the guiding valve 82 is swingably supported in the A-B direction in the figure and make a transition between an inclined state where it is inclined relative to the axial direction of the tube main body 64 (passage 66) and occludes the passage 66 that is positioned more distally than the position where the guiding valve 82 is provided, as shown in FIG. 6A, and a parallel state (retracted state) where it is substantially parallel to the axial direction of the tube main body 64 (passage 66) and releases the passage 66 that is positioned more distally than the position where the guiding valve 82 is provided, as shown in FIG. 6B. Moreover, the guiding valve 82 is urged in A direction, and unless tractive force is applied to the guiding valve 82 by a manipulating wire 90 mentioned later, the guiding valve 82 is held in the inclined state as shown in FIG. 6A. In addition, in the inclined state, the distal end portion of the guiding valve 82 comes into contact with the inner wall surface of the passage 66 as shown in FIG. 5 to regulate further rotation in A direction. Moreover, urging means urging the guiding valve 82 in the predetermined direction is not limited to the helical torsion coil spring.

On the other hand, the guiding valve 82 is pulled in B direction by the manipulating wire 90. For example, the manipulating wire 90 is wound on the shaft pin 84 to be attached in such a direction that a wound amount of the manipulating wire 90 is more in the inclined state of the guiding valve 82 than in the parallel state thereof. Thereby, in a state where the manipulating wire 90 is slacked off, the guiding valve 82 takes the inclined state in FIG. 6A, and when the manipulating wire 90 is proximally pulled, the guiding valve 82 rotates in B direction to take the parallel state in FIG. 6B.

As shown in FIG. 5, the manipulating wire 90 passes through the inside of a wire channel 92 extending in the sidewall portion 65 of the tube main body 64 along the axial direction (longitudinal direction), and the distal end portion of the manipulating wire 90 is fed from the wire channel 92 into the passage 66 in the vicinity position of the guiding valve 82 to be attached to the shaft pin 84 of the guiding valve 82. Moreover, as shown in FIG. 1, a wire tube 94 having a channel in communication with the wire channel 92 extends to be provided and the proximal end side of the manipulating wire 90 is extended from a proximal end opening of the wire tube 94. Accordingly, by grasping the proximal end side of the manipulating wire 90 which extends from the proximal end opening of the wire tube 94 and performing operation of pulling or slacking off the proximal end side, an operator can perform switching of the guiding valve 82 between the parallel state and the inclined state as mentioned above.

In the case where the insertion part 12 of the endoscope 10 is inserted into the passage 66 of the tube main body 64 from the proximal end opening part 62A of the grasping part 62, when the manipulating wire 90 is pulled to allow the guiding valve 82 to be in the parallel state, the insertion part 12 can be inserted to the distal end of the passage 66 and the insertion part 12 can be fed from the distal end opening part 67. In addition, once passing the insertion part 12 through the position of the guiding valve 82, the manipulating wire 90 is not needed to be pulled after that but may be slacked off. On the other hand, when the manipulating wire 90 is slacked off before passing the insertion part 12 through the position of the guiding valve 82 to allow the guiding valve 82 to be in the inclined state, the insertion part 12 is guided in the direction of the sidewall opening part 68 by the guiding valve 82, and thereby, the insertion part 12 can be easily fed from the sidewall opening part 68.

In addition, the guiding valve 82 may have a size and a shape to the extent that in the inclined state, the insertion part 12 is not passed through spacing between the guiding valve 82 and the inner wall of the passage 66 (inner surface of the sidewall portion 65 of the tube main body 64) to the passage 66 that is positioned more distally than the guiding valve 82.

Furthermore, as shown in FIG. 3, FIG. 4, FIG. 6A and FIG. 6B, an inflatable and deflatable balloon 96 is attached to a sidewall outer peripheral surface that is positioned more distally than the sidewall opening part 68 of the tube main body 64. This balloon 96 is in communication with a fluid channel 98 extending along the axial direction in the sidewall portion 65 of the tube main body 64, and the fluid channel 98 is in communication with a channel in a tube 74 shown in FIG. 1 which extends to the proximal end side of the tube main body 64. An end of the tube 74 is provided with a connector 76 and, by the connector 76, the tube 74 is connected to a balloon controlling device 78.

Figure 7:
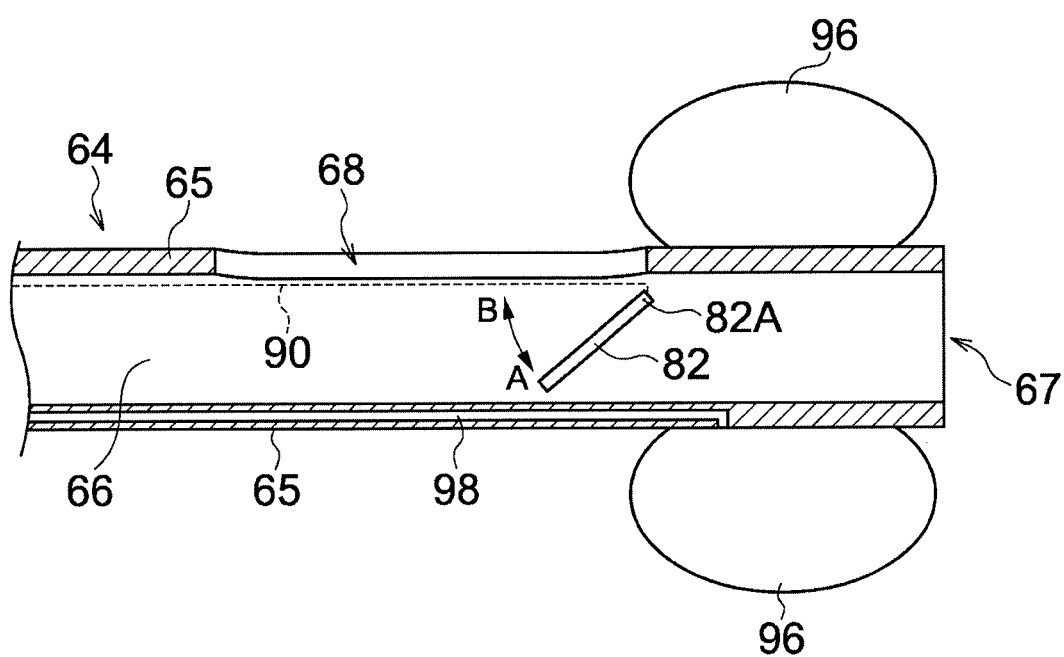
FIG. 7 is a lateral cross-sectional view showing a state where a balloon of the insertion assisting tool inflates.

The balloon controlling device 78 is a device supplying a fluid such as air to the channel in the tube 74 connected by the connector 76 and also sucking the fluid from the channel in the tube 74. The balloon controlling device 78 supplies the fluid to the channel in the tube 74, and thereby allowing the fluid supplied to the channel to flow through the fluid channel 98 of the tube main body 64 and to be injected into the balloon 96. This causes the balloon 96 to inflate annularly around the tube main body 64 as shown in FIG. 7. On the other hand, the balloon controlling device 78 sucks the fluid from the channel in the tube 74, and thereby allowing the balloon 96 to discharge the fluid injected into the balloon 96 into the fluid channel 98 of the tube main body 64, so that the balloon controlling device 78 allows the fluid to flow through the fluid channel 98 and the channel in the tube 74 and to be sucked. Thus, the balloon 96 is configured to be deflatable.

Next, an operating method of the endoscopic device configured as mentioned above is described with reference to FIG. 8 to FIG. 10. Herein, a case where the insertion part 12 of the endoscope 10 is inserted into a biliary tract 104 is described as one example, whereas a case of insertion into a pancreatic duct 106 can also be performed similarly.

Figure 8:
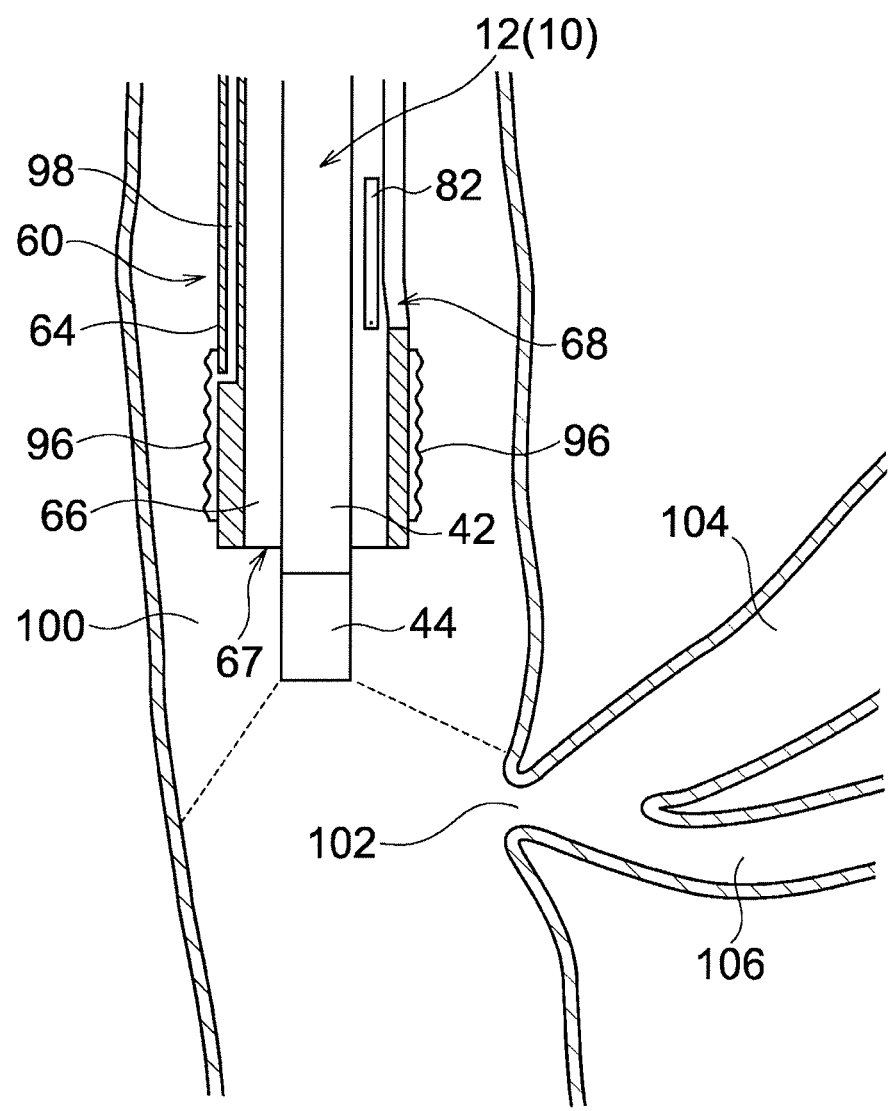
FIG. 8 is an explanatory drawing showing procedure of inserting the insertion part of the endoscope into the biliary tract using the insertion assisting tool.

First, the insertion part 12 of the endoscope 10 is covered with the insertion assisting tool 60, the insertion part 12 is passed into the passage 66 of the tube main body 64 as shown in FIG. 8, and in this state, the insertion part 12 and the tube main body 64 are inserted through a patient's mouth and inserted into a duodenum 100 through the stomach, while the angle knobs 36, 36 of the endoscope 10 are operated to appropriately perform bending operation of the bending part 42. At this stage, by pulling the manipulating wire 90 toward the proximal end side, the guiding valve 82 has been allowed to be in the parallel state as shown in FIG. 6B, the insertion part 12 has been put forward into the passage 66 that is positioned more distally than the guiding valve 82, and the distal end of the insertion part 12 has been fed from the distal end opening part 67. Moreover, the balloon 96 has been in a deflated state.

Figure 9:
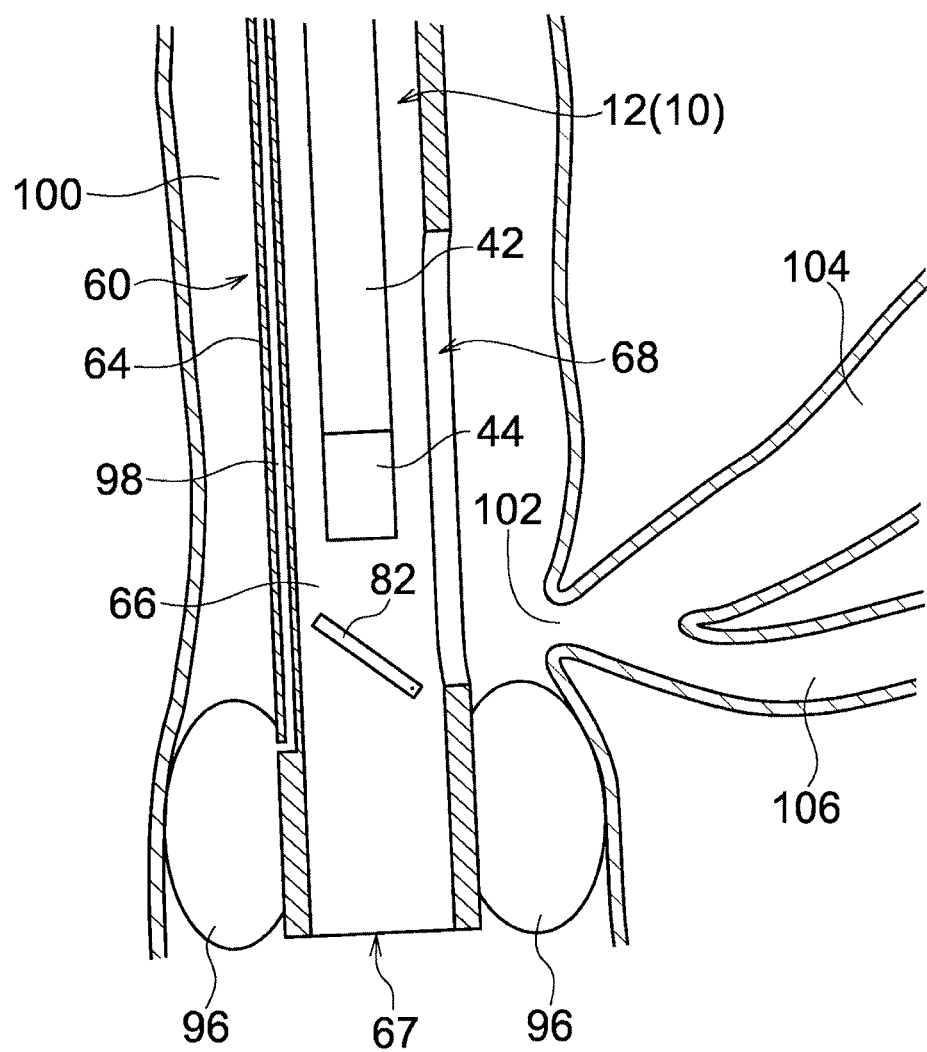
FIG. 9 is an explanatory drawing showing procedure of inserting the insertion part of the endoscope into the biliary tract using the insertion assisting tool.

Next, after a major duodenal papilla 102 is confirmed through an observation image observed by the observation optical system 52 on the distal end face 45 of the endoscope 10, the insertion assisting tool 60 is put further forward into a deep portion (distal end side) of the duodenum 100, and positioning is performed so as to allow the sidewall opening part 68 of the tube main body 64 to face the major duodenal papilla 102, as shown in FIG. 9. Then, the balloon controlling device 78 injects the fluid into the balloon 96 to inflate the balloon 96 and to bring the balloon 96 into close contact with an inner wall of the duodenum 100, allowing to fix the position of the tube main body 64 in the duodenum 100 and to hold the sidewall opening part 68 of the tube main body 64 at a position opposite to the major duodenal papilla 102.

Figure 10:
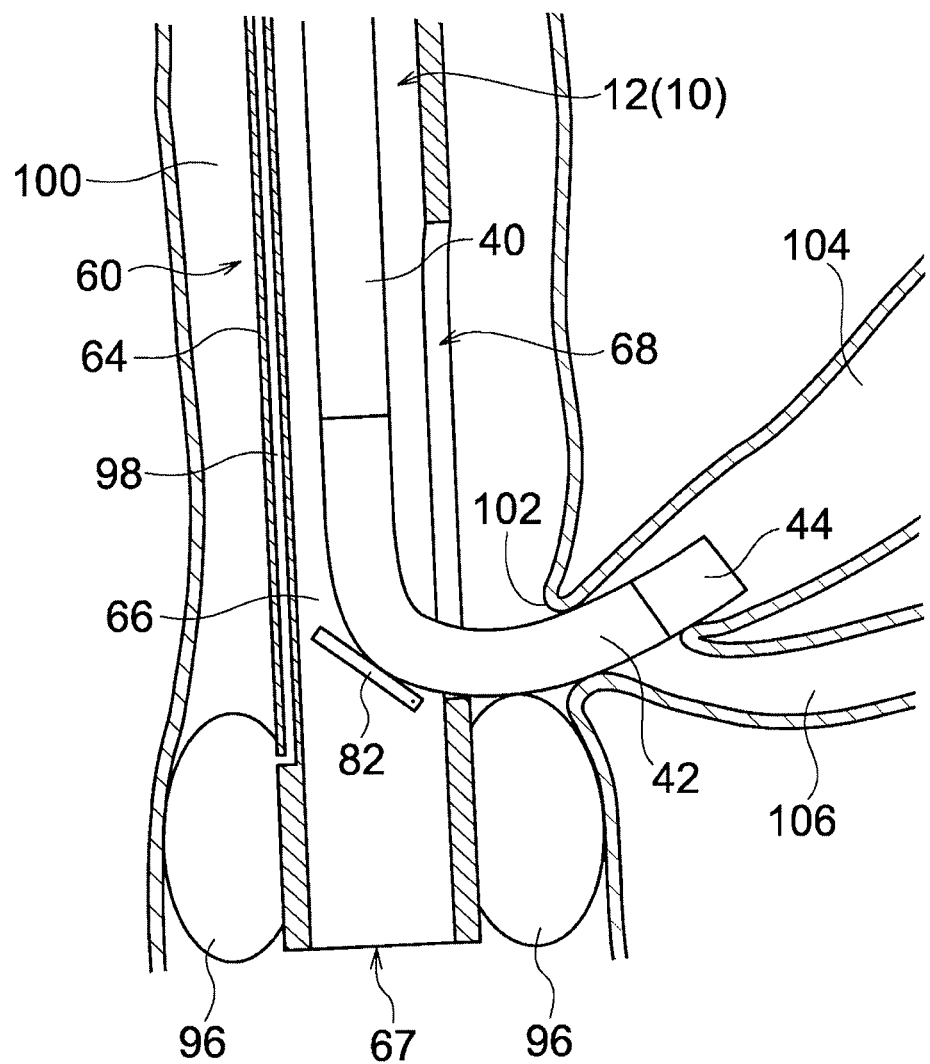
FIG. 10 is an explanatory drawing showing procedure of inserting the insertion part of the endoscope into the biliary tract using the insertion assisting tool.

Next, the insertion part 12 is put further forward while undergone bent operation, the distal end of the insertion part 12 is fed from the sidewall opening part 68 of the tube main body 64 as shown in FIG. 10, and the distal end thereof is inserted into the biliary tract (common bile duct) 104 from the major duodenal papilla 102. At this stage, by slacking off the manipulating wire 90 to allow the guiding valve 82 to be in the inclined state as shown in FIG. 6A, when putting the insertion part 12 further forward, the insertion part 12 is guided by the guiding valve 82 to be easily and smoothly fed from the sidewall opening part 68. Moreover, when the distal end side of the insertion part 12 is bent into a J-shape by the bending part 42 and inserted into the biliary tract 104, the distal end of the insertion part 12 is guided while the bending part 42 is received and supported on the outer surface of the balloon 96, and therefore, force to the insertion direction works effectively and the distal end of the insertion part 12 can be easily inserted into the biliary tract 104. Then, the distal end of the insertion part 12 can be put further forward gradually into a deep portion thereof.

As described above, according to the insertion assisting tool 60 of the embodiment, using the guiding valve 82 of the tube main body 64, the insertion part 12 of the endoscope 10 can be easily and smoothly fed from the sidewall opening part 68 provided to the sidewall portion 65 of the tube main body 64. Moreover, the insertion part 12 can be easily inserted into the biliary tract 104 or the pancreatic duct 106, while received and supported on the inflated balloon 96. Furthermore, when the insertion part 12 is fed from the sidewall opening part 68, since the guiding valve 82 is fixedly held in the inclined state by causing the proximal end side of the guiding valve 82 to come into contact with the inner wall surface of the tube main body 64, the distal end side of the guiding valve 82 (end part of the guiding valve 82 being on the distal end side of the tube main body 64) being the rotation fulcrum as in the embodiment, compared with a case where the distal end side of the guiding valve 82 is caused to face the sidewall opening part 68 and fixedly held in the inclined state, the proximal end side of the guiding valve 82 being the rotation fulcrum, there is no need for any special locking mechanism or the like for regulating rotation of the guiding valve 82 against the load from the insertion part 12 and fixedly holding it in the inclined state, enabling the configuration to be simple.

In addition, in place of inserting the endoscope 10 into the biliary tract 104 or the pancreatic duct 106 from the major duodenal papilla 102, operations are also possible, for example, in which holding the distal end face 45 of the endoscope 10 in the state where it is put close to the vicinity of the major duodenal papilla 102, feeding a cannula from the forceps exit 58 of the endoscope 10, selectively inserting the cannula into the biliary tract 104 or the pancreatic duct 106 from the major duodenal papilla 102, and injecting contrast medium into the biliary tract 104 or the pancreatic duct 106 through the cannula, are performed in ERCP.

Moreover, when the endoscope 10 is inserted into the biliary tract 104 or the pancreatic duct 106 from the major duodenal papilla 102 and the inside of the biliary tract 104 or the inside of the pancreatic duct 106 is observed, an endoscope with a very fine insertion part that does not include any forceps channel may be used as the endoscope 10.

As above, in the embodiment, the guiding valve 82 of the tube main body 64 is urged so as to be in the inclined state as shown in FIG. 6A in a state where the manipulating wire 90 is slacked off, whereas it may be urged in the direction opposite to that in the embodiment (B direction) so as to be in the parallel state as shown in FIG. 6B in a state where the manipulating wire 90 is slacked off. In this case, for example, the manipulating wire 90 may be wound to be attached in such a direction that a wound amount the manipulating wire 90 is more in the parallel state of the guiding valve 82 than in the inclined state thereof. Thereby, in the state where the manipulating wire 90 is slacked off, the guiding valve 82 is in the parallel state as shown in FIG. 6B, and when pulling the manipulating wire 90 toward the proximal end side, the guiding valve 82 rotates to A direction so as to be in the inclined state of FIG. 6A.

Figure 11:
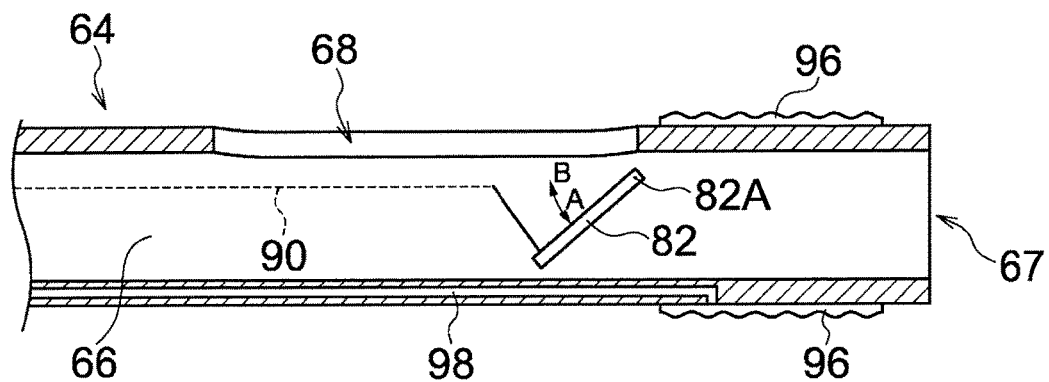
FIG. 11 is a lateral cross-sectional view showing another embodiment regarding a manipulating wire of the guiding valve of the insertion assisting tool.

Moreover, in the embodiment, the manipulating wire 90 pulling the guiding valve 82 of the tube main body 64 is attached to the shaft pin 84 of the guiding valve 82, whereas, not limited to this, it may be attached to the guiding valve 82. For example, as shown in FIG. 11, when the guiding valve 82 is urged in A direction, the manipulating wire 90 which is passed through the wire channel extending in the sidewall portion 65 of the tube main body 64 may be fed in the passage 66 from a position on B direction side relative to the guiding valve 82 in the inclined state, and, the distal end of the manipulating wire 90 may be fixedly attached to a distal end portion of the guiding valve 82. Moreover, switching between the inclined state and the parallel state may be performed by pushing and pulling operation of one or more manipulating wires without the biasing means urging the guiding valve 82 to A direction or B direction as in the embodiment.

Moreover, in the embodiment, an aspect in which the distal end of the tube main body 64 is provided with the balloon 96 is presented, whereas the balloon 96 is not necessarily to be provided.

Next, other embodiments of the tube main body 64 of the insertion assisting tool 60 (guiding valve 82) are described. In addition, constituents to which the same reference numerals as ones for the embodiment (hereinafter referred to as a first embodiment) are attached indicate constituents with the same or similar functions as or to ones for the first embodiment and their description is omitted in the other embodiments that are described below.

Figure 12:
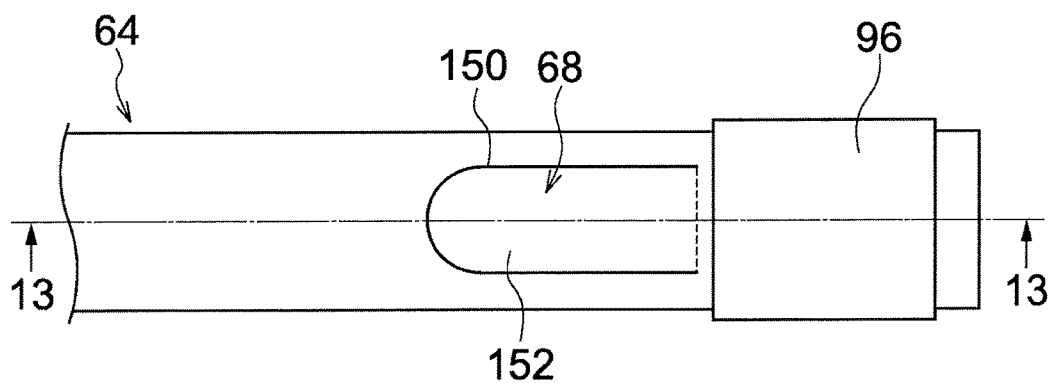
FIG. 12 is a schematic diagram (plan view) showing an exemplary configuration in the vicinity of the distal end of the insertion assisting tool according to another embodiment.
Figure 13:
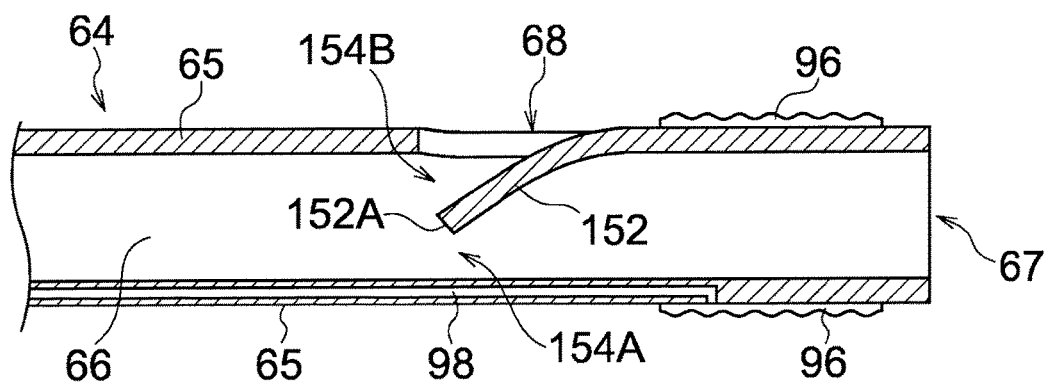
FIG. 13 is a schematic diagram (lateral cross-sectional view) showing an exemplary configuration in the vicinity of the distal end of the insertion assisting tool according to the other embodiment.

FIG. 12 and FIG. 13 are schematic diagrams showing an exemplary configuration in the vicinity of the distal end of the tube main body 64 according to a second embodiment, in which FIG. 12 is a plan view thereof and FIG. 13 is a lateral cross-sectional view (cross-sectional view taken along the line 13-13 in FIG. 12) thereof.

As shown in these figures, a notch 150 with a U-shape is made in the sidewall portion 65 of the tube main body 64 on the distal end side, a portion enclosed by the notch 150 is pushed inward in the passage 66, and thereby, a guiding valve 152 and the sidewall opening part 68 are formed. Moreover, the guiding valve 152 has curling in a portion where it is coupled with a cylindrical surface of the tube main body 64, and an end portion 152A of the guiding valve 152 (end portion which is the proximal end side of the tube main body 64) is held in the vicinity of the center of the passage 66 as shown in FIG. 13. Thereby, at the position of the end portion 152A of the guiding valve 152, a guiding port 154A which leads to the distal end opening part 67 of the tube main body 64 and a guiding port 154B which leads to the sidewall opening part 68 of the tube main body 64 are formed in the passage 66.

Figure 14A:
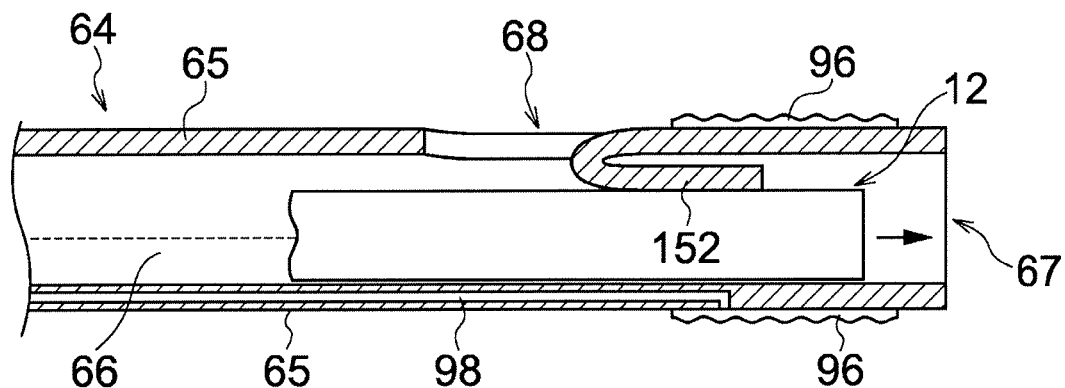
FIG. 14A is an explanatory drawing (lateral cross-sectional view) used for explaining action of a guiding valve of the insertion assisting tool in FIG. 13.

According to this configuration, when the insertion part 12 of the endoscope 10 inserted into the passage 66 of the tube main body 64 is fed from the distal end opening part 67 of the tube main body 64, by putting the distal end of the insertion part 12 further forward while bringing it close to the guiding port 154A side (exerting pushing force not less than predetermined one on the guiding valve 152), the distal end of the insertion part 12 is not guided to the sidewall opening part 68 by the guiding valve 152, for example, the guiding valve 152 is deformed as shown in FIG. 14A (deformed substantially parallelly in the axial direction of the tube main body 64 (passage 66)) to be allowed in the retracted state, and the distal end of the insertion part 12 progresses toward the distal end opening part 67 in the passage 66. In addition, depending on a diameter of the insertion part 12 or the like, there may be a case where the guiding valve 152 is not bent toward the distal end side of the tube main body 64 as shown in FIG. 14A but is retracted in a direction in which the sidewall opening part 68 is occluded.

Figure 14B:
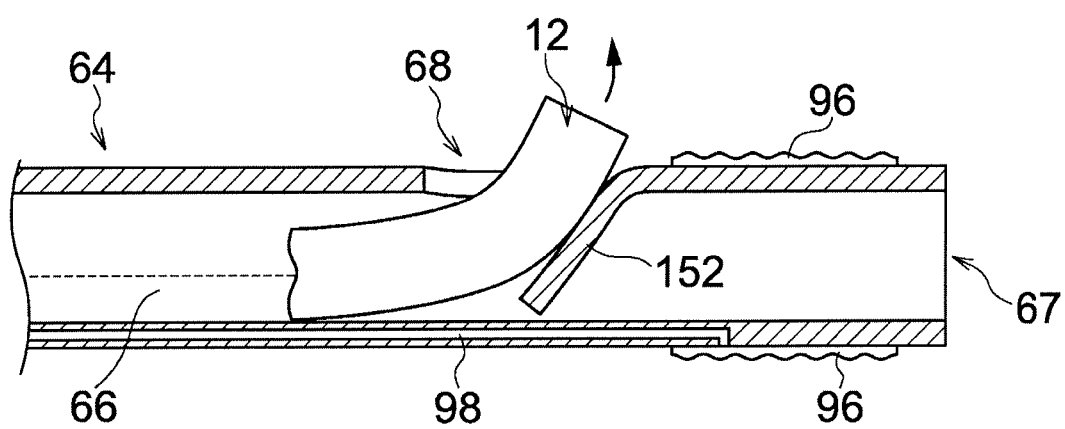
FIG. 14B is an explanatory drawing (lateral cross-sectional view) used for explaining action of the guiding valve of the insertion assisting tool in FIG. 13.

On the other hand, when the insertion part 12 is fed from the sidewall opening part 68 of the tube main body 64, by appropriately performing bending operation of the bending part 42 of the insertion part 12 while putting the distal end of the insertion part 12 further forward by bringing it close to the guiding port 154B side (not exerting pushing force not less than predetermined one on the guiding valve 152), the guiding valve 152 is further inclined relative to the axial direction of the tube main body 64 as shown in FIG. 14B, and thereby, the insertion part 12 is guided in the direction of the sidewall opening part 68 to be fed from the sidewall opening part 68.

Moreover, there is conventionally known an endoscope 10 including a balloon that is, for example, annular on an outer peripheral surface in the vicinity of a distal end of an insertion part 12 of the endoscope 10, when the insertion part 12 is inserted into the guiding port 154B, the balloon of the insertion part 12 may be inflated to incline the guiding valve 152 and to enlarge the guiding port 154B, and after that, the insertion part 12 may be guided to the sidewall opening part 68, while inflation and deflation of the balloon of the insertion part 12 is controlled.

Figure 15:
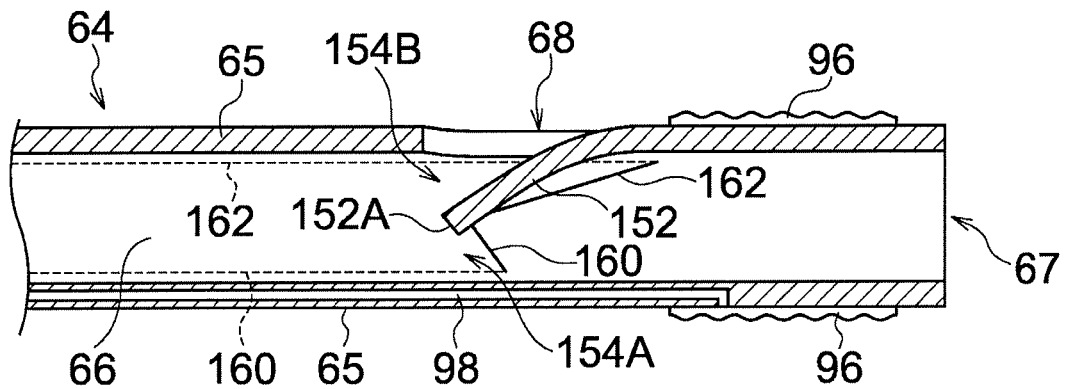
FIG. 15 is an explanatory drawing (lateral cross-sectional view) used for explaining a case of controlling the guiding valve of the insertion assisting tool in FIG. 13 with a manipulating wire.

In addition, the guiding valve 152 may also be able to be controlled with a manipulating wire. For example, as shown in FIG. 15, a distal end of a manipulating wire 160 or a manipulating wire 162 passed through the inside of a wire channel extending in the sidewall of the tube main body 64 along the axial direction may be attached to the end portion or the like of the guiding valve 152, and the guiding valve 152 may be allowed in the state shown in FIG. 13 or in the state where it is substantially parallel to the axial direction of the tube main body 64 (passage 66), in the state of the manipulating wire 160 or the manipulating wire 162 is slacked off, and may be allowed to be in the inclined state as shown in FIG. 14B upon pulling the manipulating wire 160 or the manipulating wire 162.

Figure 16:
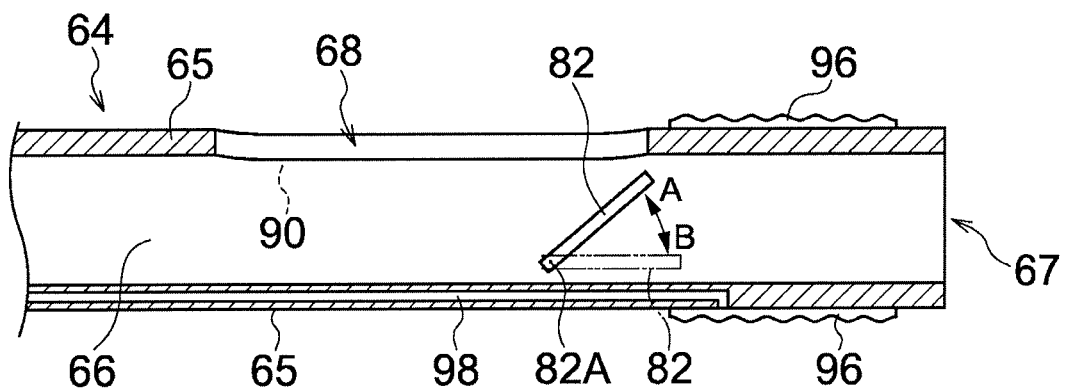
FIG. 16 is a schematic diagram (lateral cross-sectional view) showing an exemplary configuration in the vicinity of the distal end of the insertion assisting tool according to another embodiment.

FIG. 16 is a lateral cross-sectional view showing an exemplary configuration in the vicinity of the distal end of the tube main body 64 according to a third embodiment. Compared with the exemplary configuration in FIG. 4 shown according to the first embodiment, the embodiment is different in that the position of the supporting axis 82A around which the guiding valve 82 is rotatably supported is not at a position on the distal end side of the tube main body 64 but at a position on the proximal end side thereof, and in that the manipulating wire 90 is not provided; the rest being configured similarly to the first embodiment. Moreover, similarly to the first embodiment, the guiding valve 82 is urged by urging means such as a helical torsion coil spring to A direction in the figure, and as indicated by the solid line in the figure, it is allowed to be in the inclined state where it is inclined relative to the axial direction of the tube main body 64.

According to this configuration, when the insertion part 12 of the endoscope 10 inserted into the passage 66 of the tube main body 64 is fed from the distal end opening part 67 of the tube main body 64, by putting the insertion part 12 further forward against urging force of the guiding valve 82 even after the guiding valve 82 comes into contact with the distal end of the insertion part 12, the guiding valve 82 rotates in B direction, the supporting axis 82A being the fulcrum. Then, it is allowed to be in the parallel state where it is substantially parallel to the axial direction of the tube main body 64 as indicated by the broken line in the figure, and the distal end of the endoscope 10 progresses toward the distal end opening part 67 in the passage 66.

On the other hand, when the insertion part 12 is fed from the sidewall opening part 68 of the tube main body 64, by performing bending operation of the bending part 42 of the insertion part 12 to cause it to progress toward the sidewall opening part 68, the insertion part 12 is guided by the guiding valve 82 in the inclined state to be fed from the sidewall opening part 68.

Figure 17:
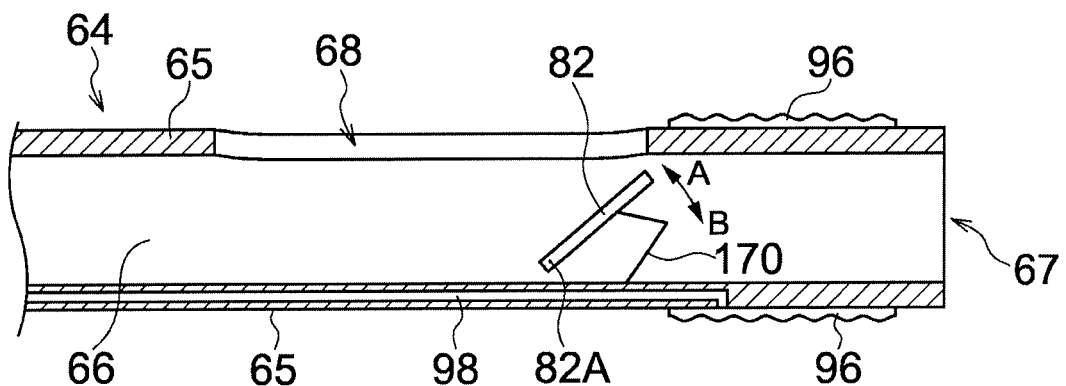
FIG. 17 is a schematic diagram (lateral cross-sectional view) showing a variation of the embodiment of FIG. 16.

In addition, it is not limited to the case where urging means such as a helical torsion coil spring is provided on supporting means supporting by the guiding valve 82 as in the first embodiment, as the urging means of the guiding valve 82 according to the embodiment, but a spring member 170 may be provided between the guiding valve 82 and the sidewall portion 65 of the tube main body 64 as shown in FIG. 17 to urge the guiding valve 82 in A direction. In this case, since urging means such as a helical torsion coil spring is not needed to be integrated with the supporting means of the guiding valve 82, one end of the guiding valve 82 can be fixedly attached directly to the sidewall portion 65 of the tube main body 64 to support the guiding valve 82, and the supporting means of the guiding valve 82 can be made simple.

Moreover, the guiding valve 82 may be rotated with the manipulating wire in B direction similarly to the first embodiment to enable transition from the inclined state to the parallel state (retracted state).

Furthermore, the guiding valve 82 may be biased by predetermined biasing means in B direction on the contrary to the embodiment in which the guiding valve 82 is rotated by the manipulating wire to A direction.

Figure 18A:
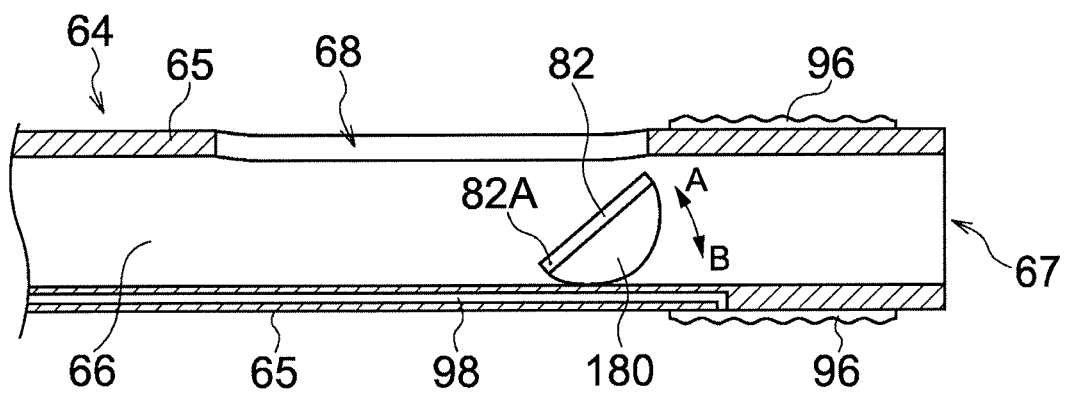
FIG. 18A is a schematic diagram (lateral cross-sectional view) showing a variation of the embodiment of FIG. 16.
Figure 18B:
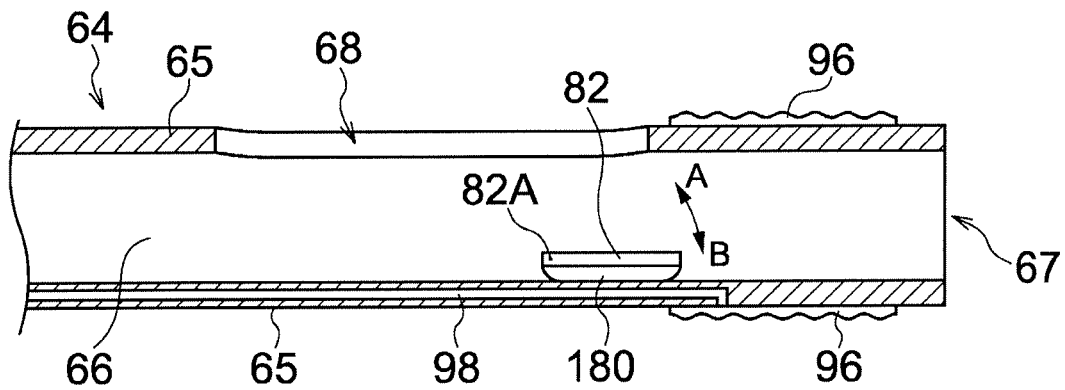
FIG. 18B is a schematic diagram (lateral cross-sectional view) showing a variation of the embodiment of FIG. 16.

Moreover, biasing means such as a helical torsion coil spring biasing the guiding valve 82 in a predetermined direction may be configured without being provided on the supporting means of the guiding valve 82, and the guiding valve 82 may be rotated by a manipulating wire or the like in a desired direction of A direction or B direction. For example, other than the method of using a manipulation wire, there is also a method of providing an inflatable and deflatable balloon 180 between the guiding valve 82 and the sidewall portion 65 of the tube main body 64 as shown in FIG. 18A. According to this method, the guiding valve 82 is allowed to be in the inclined state as shown in FIG. 18A by injecting a fluid such as air into the balloon 180, and the guiding valve 82 is allowed to be in the parallel state (retracted state) as shown in FIG. 18B by discharging the fluid from the balloon 180. In addition, similarly to the balloon 96, the balloon 180 is in communication with a fluid channel extending in the sidewall of the tube main body 64 along the axial direction, and by the fluid channel connected to the balloon controlling device, the fluid is injected or discharged. As above, when biasing means is not integrated with the supporting means of the guiding valve 82, one end of the guiding valve 82 can be fixedly attached directly to the sidewall portion 65 of the tube main body 64 to support the guiding valve 82, and the supporting means of the guiding valve 82 can be made simple.

Also in the second and third embodiments above, similarly to the first embodiment, the balloon 96 at the distal end of the tube main body 64 is not necessarily provided.

As above, although the insertion assisting tool for an endoscope according to the present invention has been described in detail, the present invention is not limited to the above examples, but it is needless to say that various modifications and variations may be made within the spirit and scope of the present invention.

REFERENCE SIGNS LIST

10: Endoscope; 12: Insertion part; 14: Hand operating part; 16: Universal cable; 36: Angle knob; 40: Flexible part; 42: Bending part; 44: Distal end portion; 45: Distal end face; 46: Forceps entrance; 52: Observation optical system; 58: Forceps exit; 60: Insertion assisting tool; 62: Grasping part; 62A: Proximal end opening part; 64: Tube main body; 66: Passage; 67: Distal end opening part; 68: Sidewall opening part; 74: Tube; 76: Connector; 78: Balloon controlling device; 82, 152: Guiding valve; 82A: Supporting axis; 84: Shaft pin; 86: Index; 88: Shaft receiving member; 90, 160, 162: Manipulating wire; 92: Wire channel; 94: Wire tube; 96, 180: Balloon; 98: Fluid channel; 100: Duodenum; 102: Major duodenal papilla; 104: Biliary tract; 106: Pancreatic duct

The invention claimed is:

1. An insertion assisting tool for an endoscope comprising:
    a flexible tubular body having an endoscope insertion passage;
    a distal end opening provided at a distal end of the flexible tubular body in a longitudinal axis direction of the flexible tubular body, the distal end opening from which an insertion part of the endoscope inserted into the endoscope insertion passage can be led out;
    a notch formed in a sidewall of the flexible tubular body, the notch being a sidewall opening from which the insertion part of the endoscope inserted into the endoscope insertion passage can be led out; and
    a flexible flap integral with the sidewall of the flexible tubular body via a living hinge and having a shape which is complementary with the notch,
    wherein one end of the flexible flap is connected to the flexible tubular body and another end of the flexible flap is a free end,
    the flexible flap is deformable between a guide state where the flap guides the endoscope insertion part to the sidewall opening part and a retracted state where the flexible flap is retracted from the guide state, and
    further comprising a manipulating wire configured to manipulate the flexible flap to be deformed between the guide state and the retracted state.

2. The insertion assisting tool for an endoscope according to claim 1, wherein
    the flexible flap has curling to an endoscope insertion passage side.

* * * * *